(12) United States Patent
Dausch et al.

(10) Patent No.: US 8,624,469 B2
(45) Date of Patent: Jan. 7, 2014

(54) MICROMACHINED ULTRASONIC TRANSDUCER WITH AIR-BACKED CAVITY AND ELECTRICAL CONNECTION

(75) Inventors: David Dausch, Raleigh, NC (US); Jim Carlson, Durham, NC (US); Christopher Brewer Sanders, Wake Forest, NC (US); Scott H. Goodwin, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 13/643,649

(22) PCT Filed: Apr. 22, 2011

(86) PCT No.: PCT/US2011/033579
§ 371 (c)(1),
(2), (4) Date: Feb. 15, 2013

(87) PCT Pub. No.: WO2011/139602
PCT Pub. Date: Nov. 10, 2011

(65) Prior Publication Data
US 2013/0200753 A1    Aug. 8, 2013

Related U.S. Application Data

(60) Provisional application No. 61/329,258, filed on Apr. 29, 2010.

(51) Int. Cl.
*H01L 41/08* (2006.01)
*A61B 8/00* (2006.01)

(52) U.S. Cl.
CPC ............. *A61B 8/4494* (2013.01); *A61B 8/4444* (2013.01)
USPC ............................ 310/334; 600/437; 600/459

(58) Field of Classification Search
USPC .................................. 310/334; 600/437, 459
See application file for complete search history.

(56) References Cited

U.S. PATENT DOCUMENTS

| | | | |
|---|---|---|---|
| 6,308,389 B1 | 10/2001 | Tezuka | |
| 7,143,487 B2 * | 12/2006 | Kikuchi et al. | 29/25.35 |
| 7,449,821 B2 * | 11/2008 | Dausch | 310/364 |
| 8,378,436 B2 * | 2/2013 | Ezaki | 257/416 |
| 2006/0238067 A1 | 10/2006 | Dausch | |
| 2007/0299345 A1 * | 12/2007 | Adachi et al. | 600/459 |
| 2009/0001853 A1 | 1/2009 | Adachi | |
| 2011/0257532 A1 * | 10/2011 | Sasaki | 600/459 |
| 2012/0319535 A1 * | 12/2012 | Dausch | 310/365 |

* cited by examiner

*Primary Examiner* — J. San Martin
(74) *Attorney, Agent, or Firm* — Womble Carlyle Sandridge & Rice, LLP

(57) ABSTRACT

A method and associated apparatus directed to a piezoelectric micromachined ultrasonic transducer (pMUT) defining an air-backed cavity are provided. A first via defined by a device substrate and associated dielectric layer, and extending to the first electrode, is substantially filled with a first conductive material. A support member engaged with the device substrate defines a second via extending to the first conductive material. The second via has a second conductive material disposed thereon, forms an electrically-conductive engagement with the first conductive material, and extends outwardly of the second via to be accessible externally to the support member. A connective element extends through a third via defined by a connection support substrate and is in electrically-conductive engagement with the second conductive material, wherein one of the connective element and connection support substrate is bonded to one of the support member and second conductive material by a bonding material engaged therebetween.

10 Claims, 14 Drawing Sheets

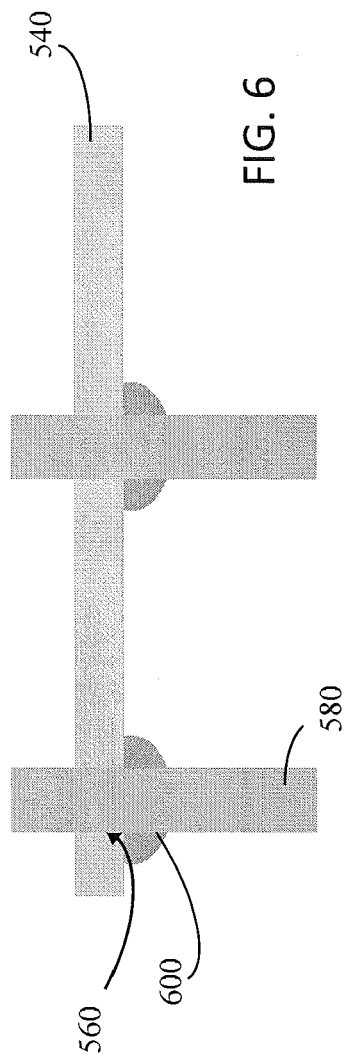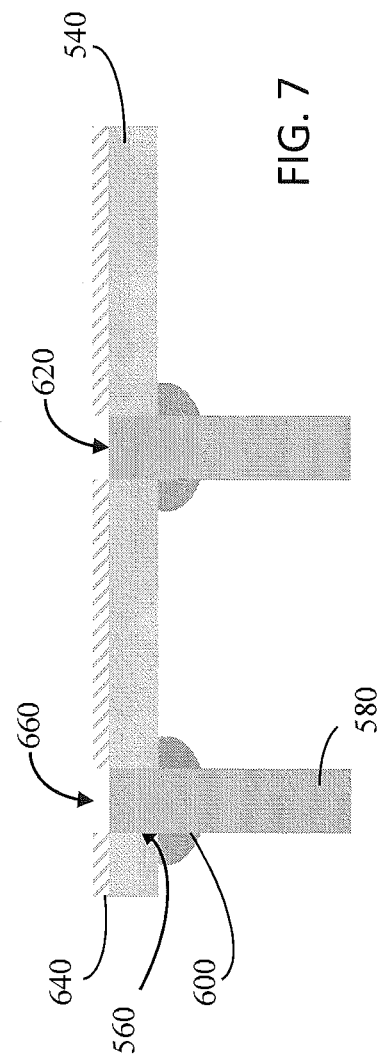

Figure 1:
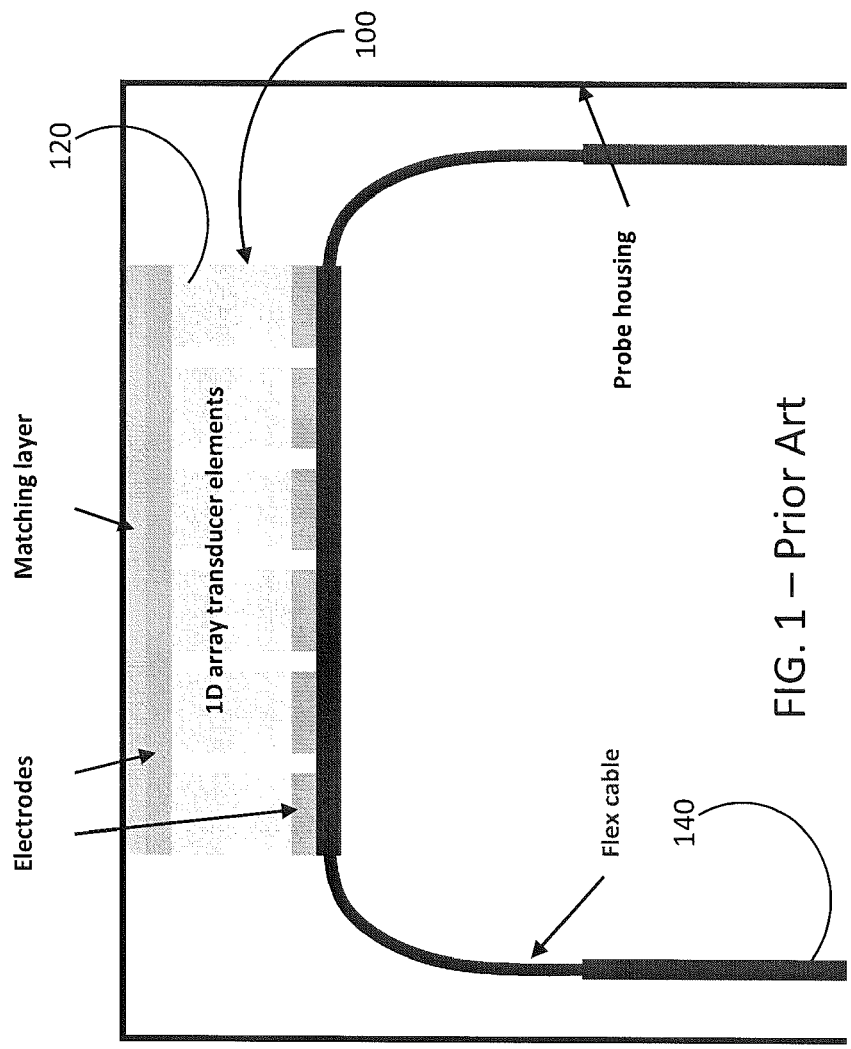

MICROMACHINED ULTRASONIC TRANSDUCER WITH AIR-BACKED CAVITY AND ELECTRICAL CONNECTION

BACKGROUND OF THE DISCLOSURE

1. Field of the Disclosure

Aspects of the present disclosure relate to ultrasonic transducers, and, more particularly, to methods of forming a connection with a piezoelectric micromachined ultrasonic transducer defining an air-backed cavity, and associated apparatuses.

2. Description of Related Art

Some micromachined ultrasonic transducers (MUTs) may be configured, for example, as a piezoelectric micromachined ultrasonic transducer (pMUT) as disclosed in U.S. Pat. No. 7,449,821 assigned to Research Triangle Institute, also the assignee of the present disclosure, which is also incorporated herein in its entirety by reference.

The formation of pMUT device, such as the pMUT device defining an air-backed cavity as disclosed in U.S. Pat. No. 7,449,821, may involve the formation of an electrically-conductive connection between the first electrode (i.e., the bottom electrode) of the transducer device, wherein the first electrode is disposed within the air-backed cavity of the pMUT device, and the conformal metal layer(s) applied to the air-backed cavity for providing subsequent connectivity, for example, to an integrated circuit ("IC") or a flex cable.

In some instances, one or more pMUTs, for example, arranged in a transducer array, may be incorporated into the end of an elongate catheter or endoscope. In those instances, for a forward-looking arrangement, the transducer array of pMUT devices must be arranged such that the plane of the piezoelectric element of each pMUT device is disposed perpendicularly to the axis of the catheter/endoscope. Where the transducer array is a one-dimensional (1D) array, external signal connections to the pMUT devices may be accomplished by way of a flex cable spanning the series of pMUT devices in the transducer array so as to be in electrical engagement with (i.e., bonded to) each pMUT device via the conformal metal layer thereof. For instance, in one exemplary 1D transducer array 100 (e.g., 1×64 elements), pMUT devices forming the array elements 120 may be attached directly to a flex cable 140, with the flex cable 140 including one electrically-conductive signal lead per pMUT device, plus a ground lead. For a forward-looking transducer array, the flex cable 140 is bent about the opposing ends of the transducer array such that the flex cable 140 can be routed through the lumen of the catheter/endoscope which, in one instance, may comprise an ultrasound probe. However, for a forward-looking transducer array in a relatively small catheter/endoscope, such an arrangement may be difficult to implement due to the severe bend requirement for the flex cable (i.e., about 90 degrees) in order for the transducer array to be disposed within the lumen of the relatively small catheter/endoscope.

Moreover, for a forward-looking two-dimensional (2D) transducer array, signal interconnection with the individual pMUT devices may also be difficult. That is, in an exemplary 2D transducer array (e.g. 14×14 to 40×40 elements), there may be many more required signal interconnections with the pMUT devices, as compared to a 1D transducer array. As such, more wires and/or multilayer flex cable assemblies may be required to interconnect with all of the pMUT devices in the transducer array. However, as the number of wires and/or flex cable assemblies increases, the more difficult it becomes to bend the larger amount of signal interconnections about the ends of the transducer device to achieve the 90 degree bend required to integrate the transducer array into a catheter/endoscope. Accordingly, such limitations may undesirably limit the minimum size (i.e., diameter) of the catheter/endoscope that can readily be achieved.

Thus, there exists a need in the ultrasonic transducer art, particularly with respect to a piezoelectric micromachined ultrasound transducer ("pMUT") having an air-backed cavity, for improved methods of forming an electrically-conductive connection between the pMUT device and, for example, an integrated circuit ("IC") or a flex cable. More particularly, it would be desirable for such an electrically-conductive connection with the pMUT device to be configured to avoid bending of the flex cable/wiring about the pMUT device upon integration thereof in the tip of a probe/catheter/endoscope used, for example, in cardiovascular devices and intravascular ultrasound devices. Such solutions should desirably be effective for 2D transducer arrays, particularly 2D pMUT transducer arrays, but should also be applicable to 1D transducer arrays, and should desirably allow greater scalability in the size of the probe/catheter/endoscope having such transducer arrays integrated therein.

BRIEF SUMMARY OF THE DISCLOSURE

The above and other needs are met by aspects of the present disclosure, wherein one such aspect relates to a method of forming a connection with a piezoelectric ultrasonic transducer apparatus, with the piezoelectric ultrasonic transducer apparatus comprising a transducer device disposed on a dielectric layer on a device substrate, wherein the transducer device includes a piezoelectric material disposed between a first electrode and a second electrode. The device substrate and the dielectric layer define a first via extending to the first electrode. The first via is substantially filled with a first conductive material. The transducer device further includes a support member engaged with the device substrate and the first conductive material. The support member defines a second via extending thereto, wherein the second via has a second conductive material disposed thereon and forms an electrically-conductive engagement with the first conductive material, and wherein the second conductive material extends outwardly of the second via so as to be accessible externally to the support member. Said method comprises bonding a connection support substrate to one of the support member and the second conductive material; etching the connection support substrate to define a third via extending to the second conductive material; and bonding a connective element to the connection support substrate, with the connective element inserted into the third via and in electrically-conductive engagement with the second conductive material.

Yet another aspect of the present disclosure provides a method of forming a connection with a piezoelectric ultrasonic transducer apparatus, the piezoelectric ultrasonic transducer apparatus comprising a transducer device disposed on a dielectric layer on a device substrate, wherein the transducer device includes a piezoelectric material disposed between a first electrode and a second electrode. The device substrate and the dielectric layer define a first via extending to the first electrode, wherein the first via is substantially filled with a first conductive material. The transducer device further includes a support member engaged with the device substrate and the first conductive material, and defining a second via extending thereto, wherein the second via has a second conductive material disposed thereon and forms an electrically-conductive engagement with the first conductive material. The second conductive material also extends outwardly of the second via so as to be accessible externally to the support member. Said method comprises etching a connection support substrate to define a third via extending therethrough; bonding a connective element to the connection support substrate, with the connective element inserted into and extending through the third via; and bonding one of the connective element and the connection support substrate to one of the support member and the second conductive material such that the connective element is in electrically-conductive engagement with the second conductive material.

Still another aspect of the present disclosure provides a piezoelectric ultrasonic transducer apparatus, comprising a transducer device disposed on a dielectric layer on a device substrate, wherein the transducer device includes a piezoelectric material disposed between a first electrode and a second electrode. The device substrate and the dielectric layer define a first via extending to the first electrode, wherein the first via is substantially filled with a first conductive material. The transducer device further includes a support member engaged with the device substrate and the first conductive material, and defining a second via extending thereto. The second via has a second conductive material disposed thereon, with the second conductive material forming an electrically-conductive engagement with the first conductive material. The second conductive material extends outwardly of the second via so as to be accessible externally to the support member. A connective element extends through a third via defined by a connection support substrate, wherein the connective element is in electrically-conductive engagement with the second conductive material, with one of the connective element and the connection support substrate being bonded to one of the support member and the second conductive material by a bonding material engaged therebetween.

Another aspect of the present disclosure provides a method of forming a connection with a piezoelectric ultrasonic transducer apparatus, comprising a transducer device disposed on a dielectric layer on a device substrate, wherein the transducer device includes a piezoelectric material disposed between a first electrode and a second electrode. The device substrate and the dielectric layer define a first via extending to the first electrode, wherein the first via is substantially filled with a first conductive material. The transducer device further includes a support member engaged with the device substrate and the first conductive material, and defining a second via extending thereto. The second via has a second conductive material disposed thereon and forms an electrically-conductive engagement with the first conductive material about an end wall of the second via. Said method comprises bonding a connective element to the support member, wherein the connective element is received into the second via so as to be in electrically-conductive engagement with the second conductive material and spaced apart from the end wall of the second via.

Still another aspect of the present disclosure provides a piezoelectric ultrasonic transducer apparatus, comprising a transducer device disposed on a dielectric layer on a device substrate, and including a piezoelectric material disposed between a first electrode and a second electrode. The device substrate and the dielectric layer define a first via extending to the first electrode and substantially filled with a first conductive material. The transducer device further includes a support member engaged with the device substrate and the first conductive material, and defining a second via extending thereto. The second via has a second conductive material disposed thereon and forming an electrically-conductive engagement with the first conductive material about an end wall of the second via. A connective element is received into the second via defined by a connection support substrate, and is bonded to the support member by a bonding material engaged therebetween. The connective element is in electrically-conductive engagement with the second conductive material and spaced apart from the end wall of the second via.

Aspects of the present disclosure thus address the identified needs and provide other advantages as otherwise detailed herein.

BRIEF DESCRIPTION OF THE SEVERAL VIEWS OF THE DRAWING(S)

Figure 2:
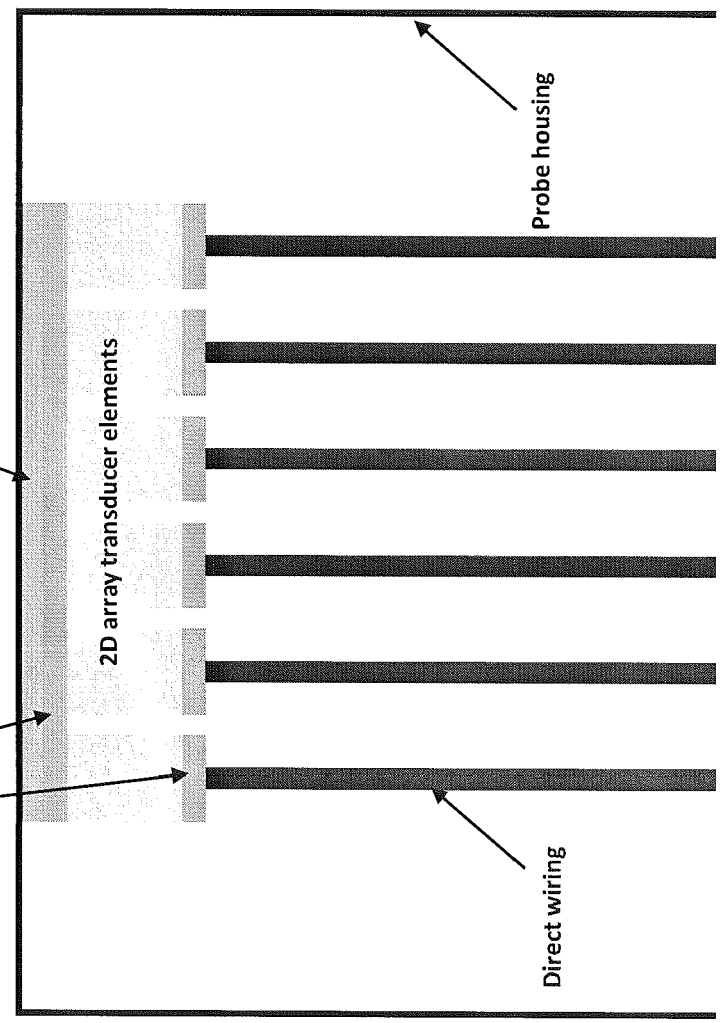
Figure 3:
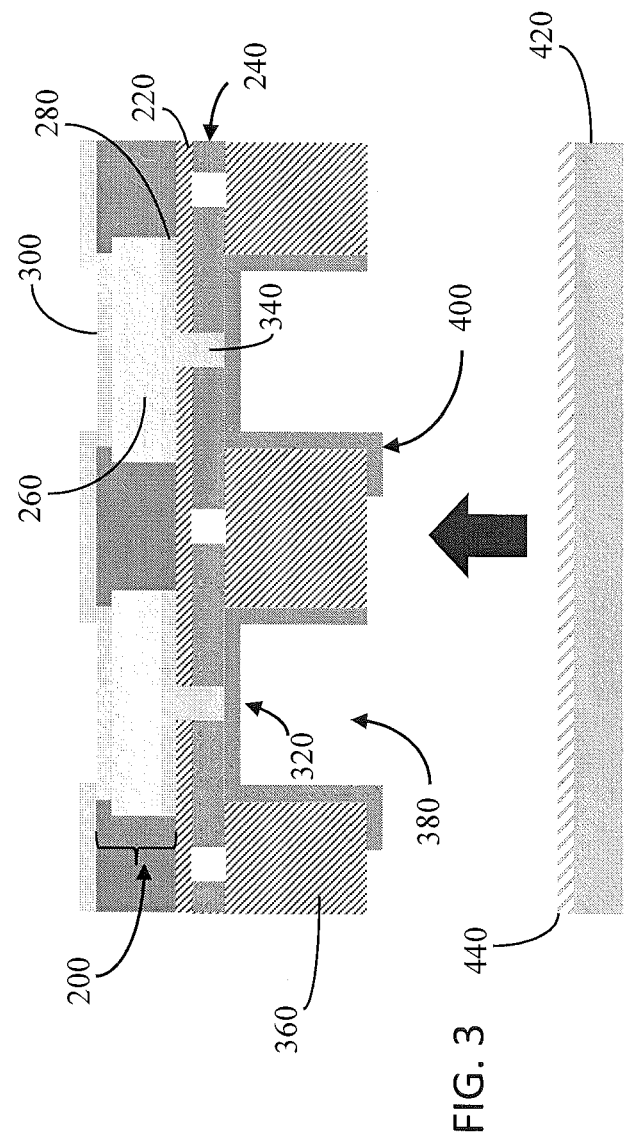
Figure 4:
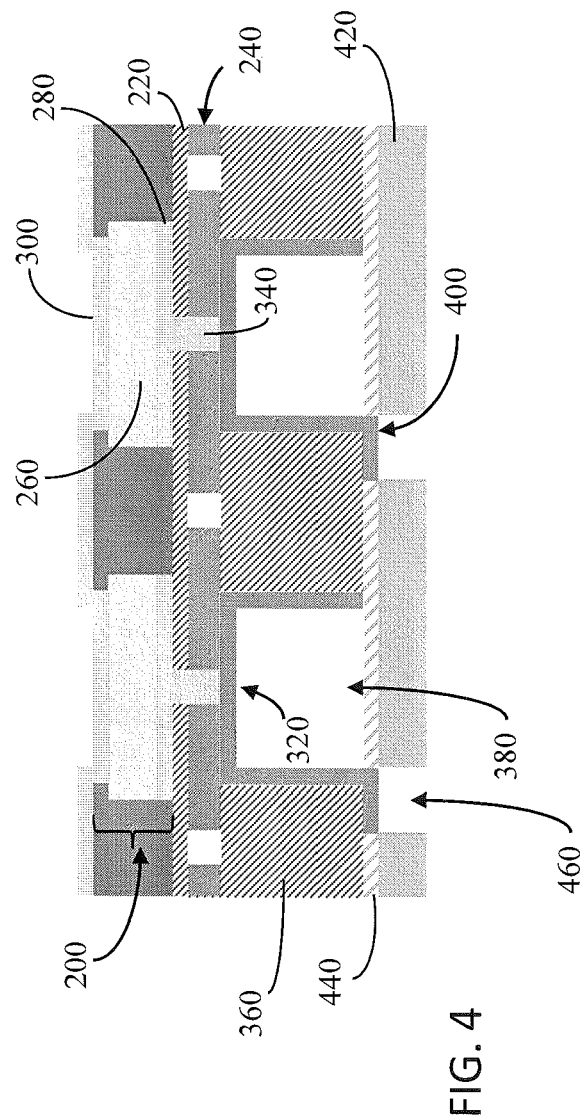
Figure 5:
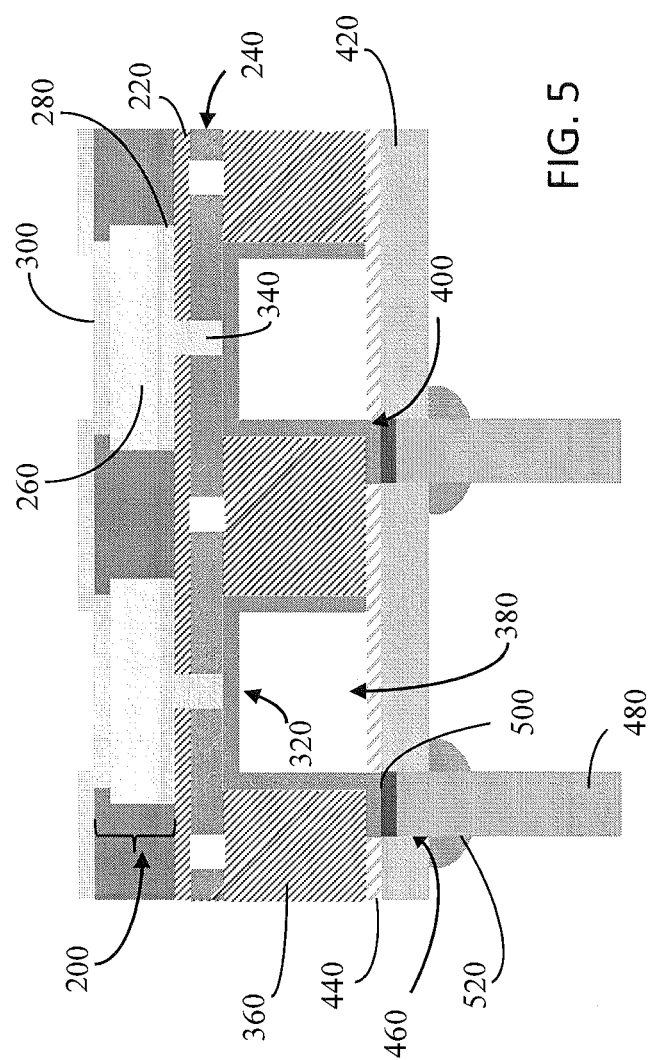
Figure 11:
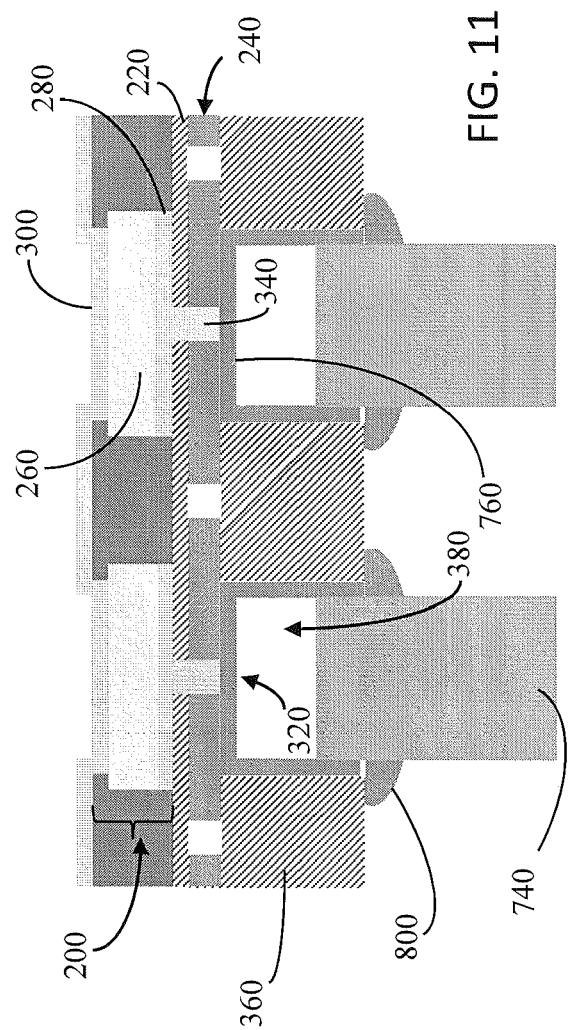
Figure 12:
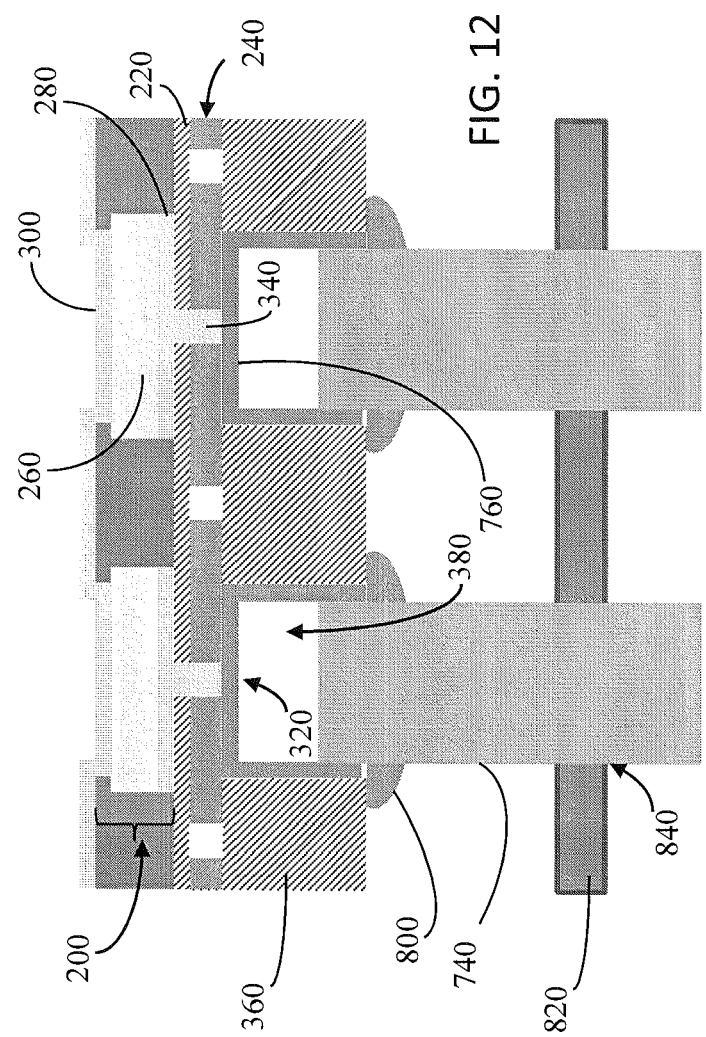
Figure 13:
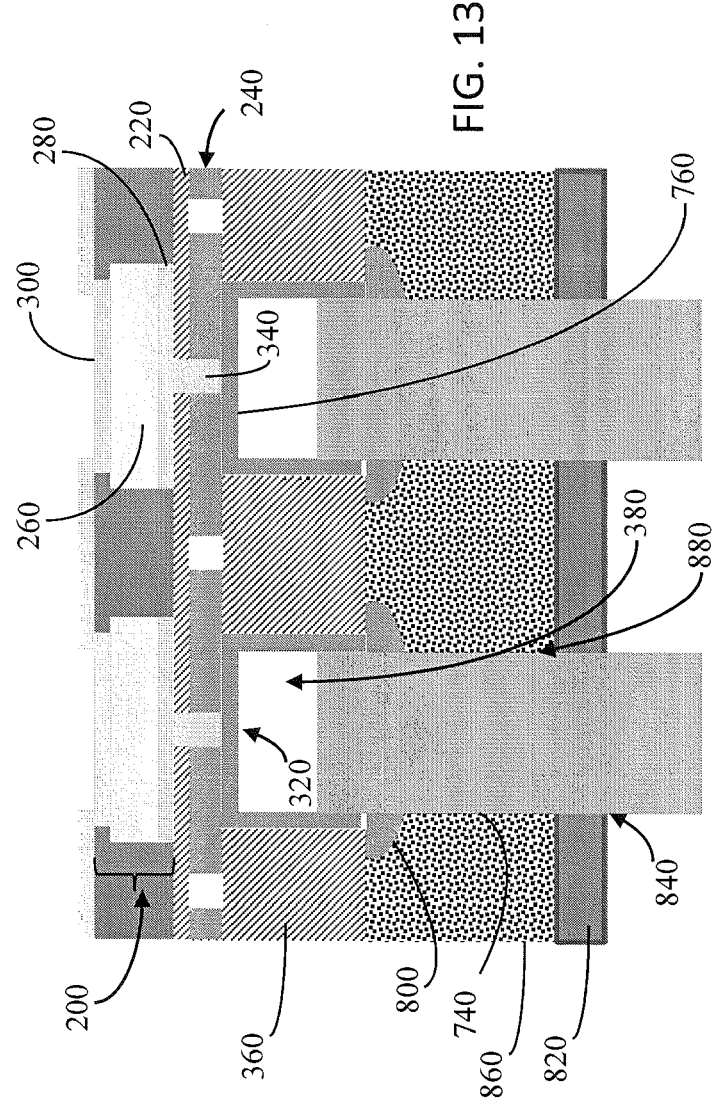
Figure 14:
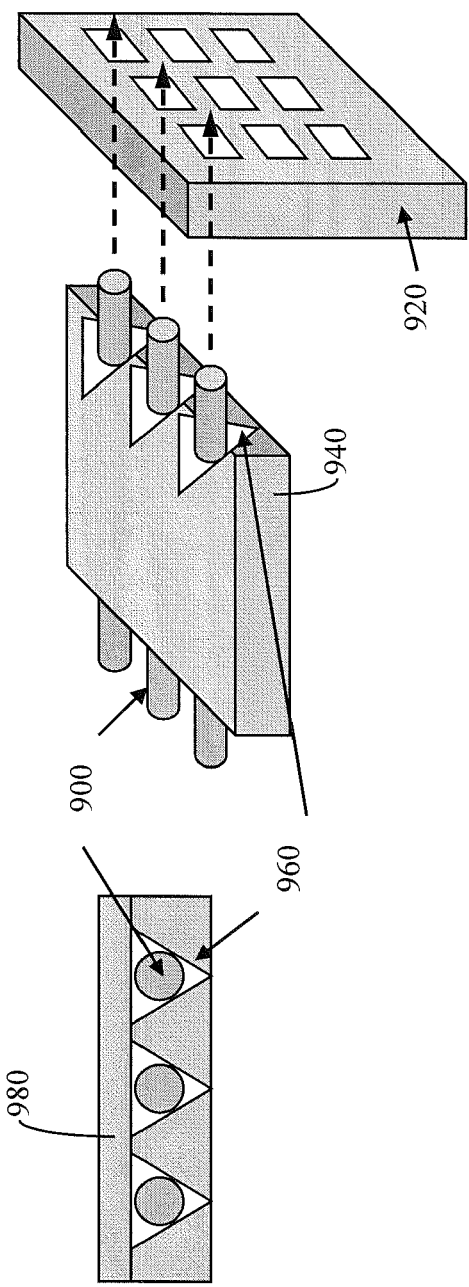
Figure 15:
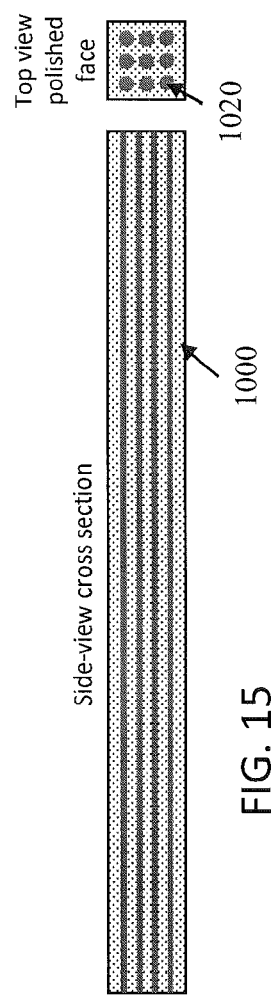
Figure 16:
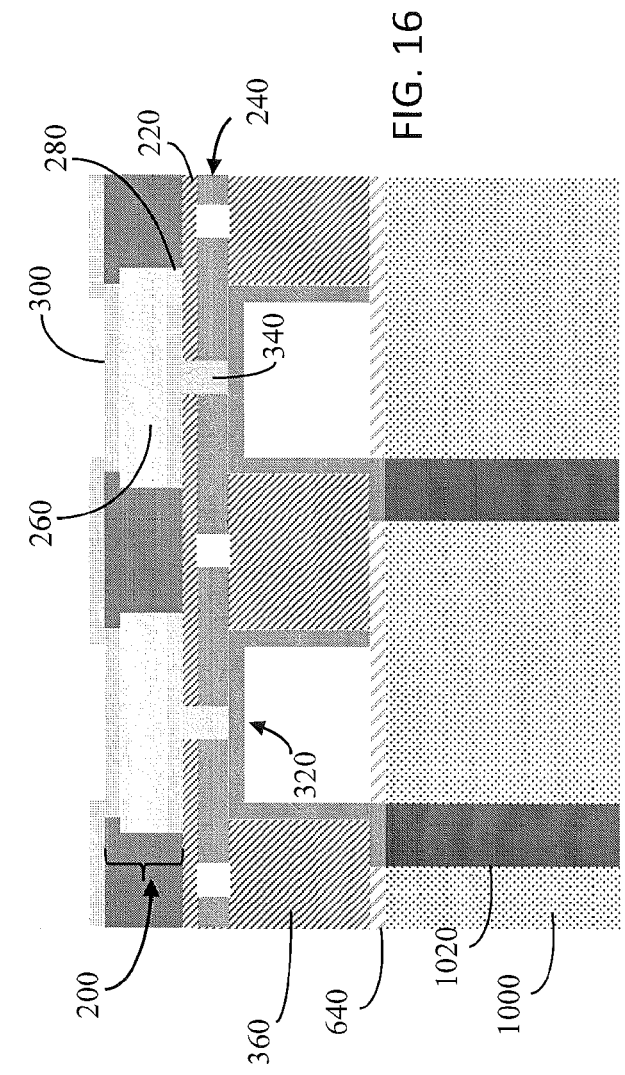

Having thus described the disclosure in general terms, reference will now be made to the accompanying drawings, which are not necessarily drawn to scale, and wherein:

FIG. 1 schematically illustrates a prior art arrangement for forming a connection with a forward-looking transducer apparatus disposed in a lumen;

FIG. 2 schematically illustrates a general arrangement for forming a connection with a forward-looking two-dimensional piezoelectric micromachined ultrasonic transducer array, according to the disclosure;

FIGS. 3-5 schematically illustrate an arrangement for forming a connection with a forward-looking two-dimensional piezoelectric micromachined ultrasonic transducer array, according to one aspect of the disclosure;

FIGS. 6-10 schematically illustrate an arrangement for forming a connection with a forward-looking two-dimensional piezoelectric micromachined ultrasonic transducer array, according to another aspect of the disclosure;

FIGS. 11-13 schematically illustrate an arrangement for forming a connection with a forward-looking two-dimensional piezoelectric micromachined ultrasonic transducer array, according to yet another aspect of the disclosure;

FIG. 14 schematically illustrates an arrangement for forming a connection with a forward-looking two-dimensional piezoelectric micromachined ultrasonic transducer array, according to still another aspect of the disclosure; and FIGS. 15 and 16 schematically illustrate an arrangement for forming a connection with a forward-looking two-dimensional piezoelectric micromachined ultrasonic transducer array, according to a further aspect of the disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as being limited to the aspects set forth herein; rather, these aspects are provided so that this disclosure will satisfy applicable legal requirements. Like numbers refer to like elements throughout.

Aspects of the present disclosure are generally applicable to ultrasonic transducers, though particular aspects are particularly directed to a piezoelectric micromachined ultrasound transducer ("pMUT") having an air-backed cavity. More particularly, aspects of the present disclosure are directed to improved methods of forming an electrically-conductive connection between a pMUT device and, for example, an integrated circuit ("IC"), a flex cable, or a cable assembly, whereby individual signal leads extend parallel to the operational direction of the transducer array to engage the respective pMUT devices in the transducer array (see generally, e.g., FIG. 2). In such aspects, a representative pMUT device, implemented in both 1D and 2D transducer arrays, as shown, for example, in FIG. 3, may comprise a transducer device 200 disposed on a dielectric layer 220 on a device substrate 240, wherein the transducer device 200 includes a piezoelectric material 260 disposed between a first electrode 280 and a second electrode 300. The device substrate 240 and the dielectric layer 220 define a first via 320 extending to the first electrode 280, wherein the first via 320 is substantially filled with a first conductive material 340. The transducer device 200 further includes a support member 360 (e.g., a silicon-on-insulator substrate) engaged with the device substrate 240 and the first conductive material 340, and defining a second via 380 extending thereto. The second via 380 has a second conductive material 400 disposed thereon, with the second conductive material 400 forming an electrically-conductive engagement with the first conductive material 340. The second conductive material 400 extends outwardly of the second via 380 so as to be accessible externally to the support member 360. Such a pMUT transducer device 200 is disclosed, for example, in co-pending U.S. Patent Application No. 61/299,514 ("Methods for Forming a Micromachined Ultrasonic Transducer, and Associated Apparatuses"), also assigned to Research Triangle Institute, and which is incorporated herein in its entirety by reference. In this regard, particular materials that can be implemented for the piezoelectric material 260 include, for example, ceramics including ZnO, AlN, LiNbO$_4$, lead antimony stannate, lead magnesium tantalate, lead nickel tantalate, titanates, tungstates, zirconates, or niobates of lead, barium, bismuth, or strontium, including lead zirconate titanate (Pb(Zr$_x$Ti$_{1-x}$)O$_3$ (PZT)), lead lanthanum zirconate titanate (PLZT), lead niobium zirconate titanate (PNZT), BaTiO$_3$, SrTiO$_3$, lead magnesium niobate, lead nickel niobate, lead manganese niobate, lead zinc niobate, lead titanate. Piezoelectric polymer materials such as polyvinylidene fluoride (PVDF), polyvinylidene fluoride-trifluoroethylene (PVDF-TrFE), or polyvinylidene fluoride-tetrafluoroethylene (PVDF-TFE) can also be used.

A method of forming an electrically-conductive connection with a pMUT device, in one such aspect of the present disclosure, is thus schematically illustrated in FIGS. 3-5. In this regard, individual signal leads extending parallel to the operational direction of the transducer array are configured to directly engage the respective pMUT devices in the transducer array. As shown in FIG. 3, a connection support substrate 420 such as, for example, a silicon substrate, may first be bonded using, for instance, an epoxy, an adhesive tape, or other appropriate adhesive material 440, to one of the support member 360 and the second conductive material 400 associated with one or more of the pMUT transducer devices 200 forming the pMUT array. More particularly, the adhesive material 440 may initially be applied to the connection support substrate 420, and then the connection support substrate 420 applied to the one of the support member 360 and the second conductive material 400 so as to be secured thereto by the adhesive material 440. In doing so, the second via 380 may remain unfilled, or may be partially or otherwise incompletely filled with an acoustic material (not shown) so as to allow the piezoelectric material to flex and generate acoustic energy when actuated via the first and second electrodes 280, 300. In some instances, the adhesive material 440 may particularly comprise a non-conductive bonding material such as, for example, an SU-8 photoimageable epoxy.

The connection support substrate 420 may then be etched, as shown in FIG. 4, to define a third via 460 extending through the adhesive material 440 to the second conductive material 400 using, for example, using a deep reactive ion etch (DRIE) process. In this manner, the second conductive material 400, in electrically-conductive engagement with the first electrode 280, is exposed through the third via 460. As shown in FIG. 5, a connective element 480 may then be bonded to the connection support substrate 420, such that the connective element 480 is inserted into the third via 460 and into electrically-conductive engagement with the second conductive material 400. The connective element 480 may be bonded to the connection support substrate 420, for instance, by a bonding material 500, such as an electrically-conductive epoxy, disposed within the third via 460, between the connective element 480 and the second conductive material 400. The bonding material 500 can be inserted into the third via 460 prior to the connective element 480 being inserted therein, or the bonding material 500 may be applied to the individual connective element 480, prior to insertion thereof into the third via 460. In some instances, the connective element 480 may comprise a fine-gauge wire (e.g. 45 AWG, about 50 μm diameter), wherein the wire may, in some instances, comprise an elongate conductor circumscribed by an insulator. In such instances, the insulator may be configured to provide electrical isolation between the conductor and the connection support substrate 420. In other instances, if the wire does not include the insulator, an insulator material (not shown) may be first deposited on the connection support substrate 420 so as to extend into the third via 460 and into proximity to the second conductive material 400, after etching the connection support substrate 420 and before bonding the connective element 480, so as to electrically isolate the conductor from the connection support substrate 420.

In some aspects, the connective element 480 may also be bonded to the connection support substrate 420 with a bonding material 520 engaged therebetween and externally to the third via 460. For example, as shown in FIG. 5, the connective element 480 may be inserted into the connection support substrate 420 and then fixed thereto with a bonding material 520, such as a non-conductive epoxy, applied around the connective element 480 on the surface of the substrate opposite the adhesive material 440. Such a fine-gauge wire may be available, for example, in the form of standard magnet wire, a micro-coaxial cable, or a micro-miniature ribbon cable.

A method of forming an electrically-conductive connection with a pMUT device, in another aspect of the present disclosure, is schematically illustrated in FIGS. 6-10. As previously disclosed, individual signal leads are arranged to extend parallel to the operational direction of the transducer array, while directly engaging the respective pMUT devices in the transducer array. As shown in FIG. 6, a connection support substrate 540 is first etched, for example, using a DRIE process, to define a third via 560 extending therethrough. A connective element 580 is then bonded to the connection support substrate 540, with the connective element 580 inserted into and extending through the third via 560. In some instances, the connective element 580 may comprise a fine-gauge wire, wherein the wire may, in some instances, comprise an elongate conductor circumscribed by an insulator. In such instances, the insulator may be configured to provide electrical isolation between the conductor and the connection support substrate 540. In other instances, if the wire does not include the insulator, an insulator material (not shown) may be first deposited on the connection support substrate 540 so as to extend through the third via 560, after etching the connection support substrate 540, so as to electrically isolate the conductor from the connection support substrate 540. In some aspects, the connective element 580 may be bonded to the connection support substrate 540 with a bonding material 600 engaged therebetween and externally to the third via 560. For example, as shown in FIG. 6, the connective element 580 may be inserted through the third via 560 defined by the connection support substrate 540 and then fixed thereto with a bonding material 600, such as a non-conductive epoxy, applied around the connective element 580 on the surface of the connection support substrate 540 opposite the surface of the connection support substrate 540 through which the connective element 580 extends.

As shown in FIG. 7, once the connective element 580 is secured to the connection support substrate 540, the surface of the connection support substrate 540 through which the connective element 580 extends is planarized, for example, by a mechanical polishing process or a chemical-mechanical polishing (CMP) process to produce a substantially planar surface having the end 620 of the connective element 580 exposed. In some instances, any gap between the connective element 580 and the wall defining the third via 560 can be filled, for example, with a non-conductive epoxy to provide a void-free, planar surface of the connection support substrate 540 for subsequent processing. The connective element 580 and/or the connection support substrate 540 is subsequently bonded to the support member 360 and/or the second conductive material 400. In one instance, a non-conductive bonding material 640 such as, for example, a spin-coated or laminate adhesive, such as SU-8 photoimageable epoxy, may be applied to the planarized surface of the connection support substrate 540. The non-conductive bonding material 640 can then be selectively removed (i.e., patterned) so as to form a fourth via 660 extending through the non-conductive bonding material 640 and exposing the end 620 of the connective element 580. In other instances, the non-conductive bonding material 640 may be pre-patterned prior to being applied to the planarized surface of the connection support substrate 540, such that the end 620 of the connective element 580 is exposed through the fourth via 660 upon application of the non-conductive bonding material 640.

Figure 8:
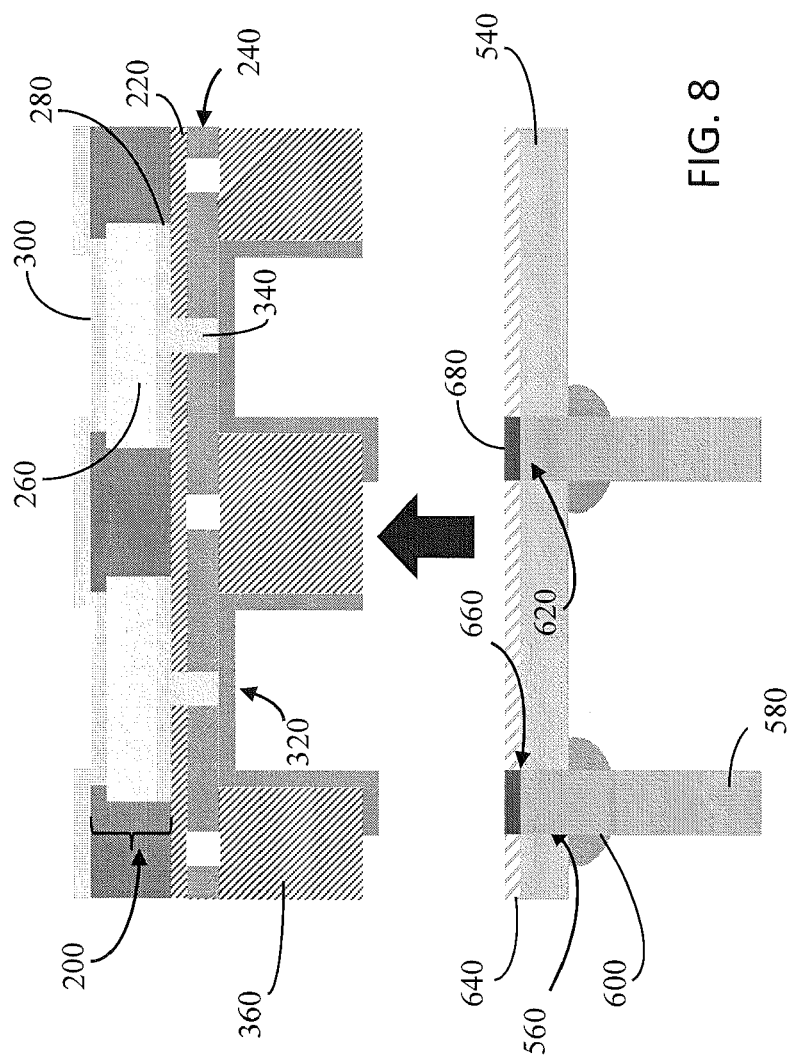
Figure 9:
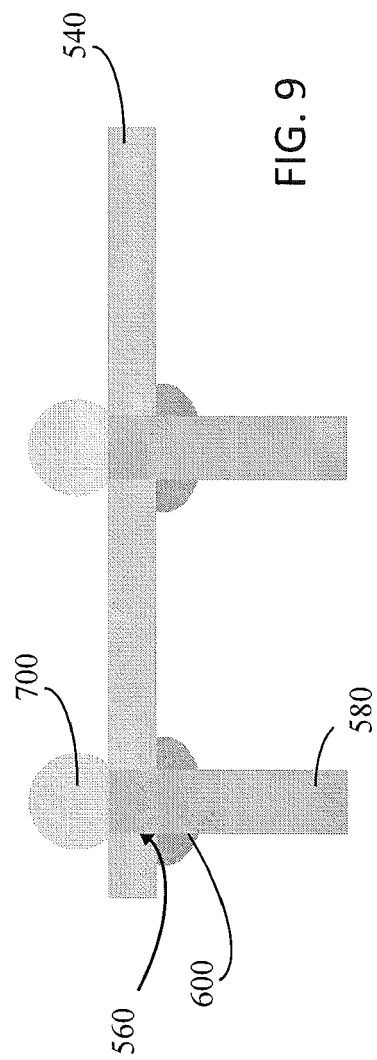

As shown in FIG. 8, a third conductive material 680 such as, for example, plated copper or an electrically-conductive epoxy, may then be deposited in the fourth via 660 such that the third conductive material 680 forms an electrically-conductive engagement with the connective element 580 and extends at least through the non-conductive bonding material 640. The connection support substrate 540 can then be bonded to at least the support member 360, such that the connective element 580 forms an electrically-conductive engagement with the second conductive material 400, for example, by curing an epoxy material comprising the non-conductive bonding material 640. In another aspect, as shown in FIG. 9, the connective element 580 is brought into electrically-conductive engagement with the second conductive material 400, for instance, via a conductive bonding material 700 disposed therebetween. In one such aspect, the conductive bonding material 700 may comprise, for example, a solder bump, as shown in FIG. 9. In such instances, the bonding may be effectuated by reflowing the solder comprising the solder bump. In another aspect, the conductive bonding material 700 may comprise metal (i.e., Au, Al, or Cu) stud bumps formed using a wire bonder or by electroplating, wherein such stud bumps can be thermo-compression bonded to provide the electrically-conductive engagement.

Figure 10:
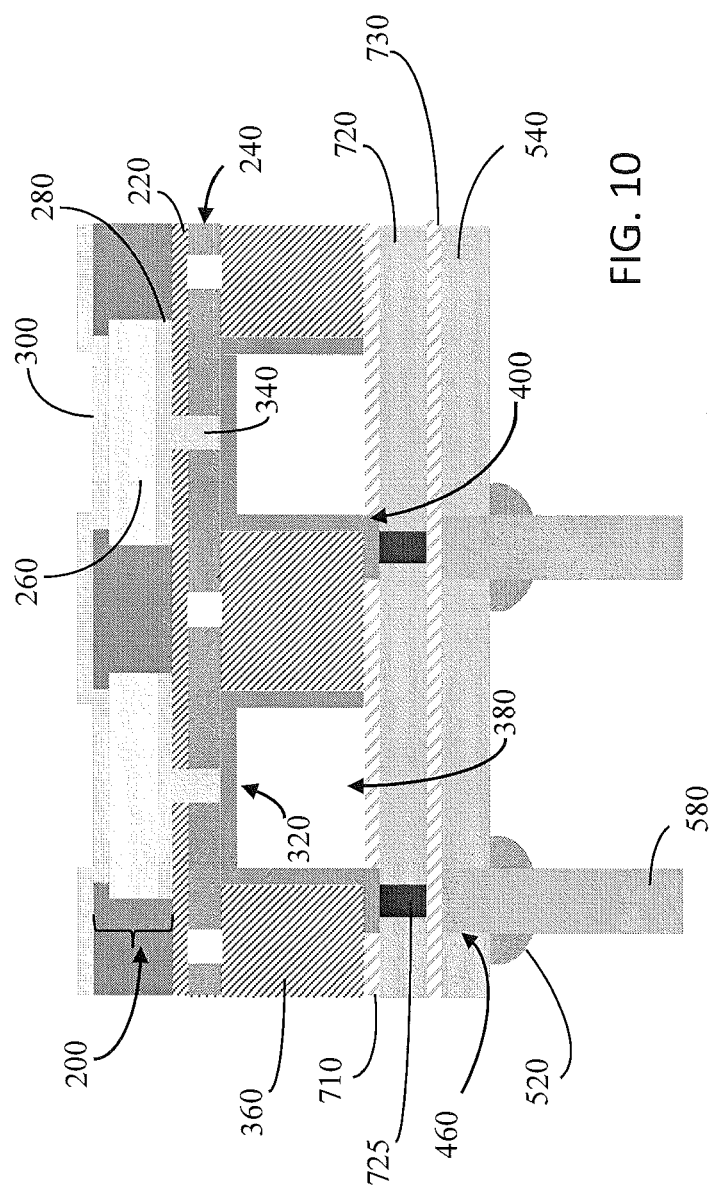

In other aspects, the connective element 580 and/or the connection support substrate 540 may be bonded to one of the support member 360 and/or the second conductive material 400 with an anisotropically-conductive epoxy 710 engaged therebetween. In this regard, an electrically-conductive engagement may be formed between the connective element 580 and the second conductive material 400, through the anisotropically-conductive epoxy 710, without such an electrically-conductive engagement extending laterally through the anisotropically-conductive epoxy 710 to other transducer devices. In still further instances, an integrated circuit device and/or a redistribution element 720 may be interposed between the connective element 580 and/or the connection support substrate 540 and the support member 360 and/or the second conductive material 400, as shown in FIG. 10. In such instances, the integrated circuit device and/or redistribution element 720 may be in electrically-conductive engagement between at least the connective element 580 and the second conductive material 400 by way of the anisotropically-conductive epoxy 710, 730 engaged respectively therebetween. The integrated circuit device and/or redistribution element 720 may also be in electrically-conductive engagement between at least the connective element 580 and the second conductive material 400, for instance, by solder bumps or by metal stud bumps. In such instances, the integrated circuit device and/or redistribution element 720 may also include one or more conductive elements extending therethrough by way of corresponding device vias 725 also defined thereby and extending therethrough, and configured to provide, for example, electrical connection between the second conductive material 400 and the connective element 580.

A method of forming an electrically-conductive connection with a pMUT device, in yet another aspect of the present disclosure, is schematically illustrated in FIGS. 11-13. As previously disclosed, individual signal leads are arranged to extend parallel to the operational direction of the transducer array, while directly engaging the respective pMUT devices in the transducer array. As shown in FIG. 11, a connective element 740 may be directly bonded to the support member 360, whereby the connective element 740 is received in the second via 380 so as to be in electrically-conductive engagement with the second conductive material 400 and spaced apart from an end wall 760 of the second via 380 where the second conductive material 400 forms the electrically-conductive engagement with the first conductive material 340. The connective element 740 is spaced apart from the end wall 760 of the second via 380 so as to allow the piezoelectric material 260 of the transducer device 200 to vibrate (i.e., to flex upon actuation via the first and second electrodes 280, 300, and thus function as intended. The connective element 740 may be bonded to the support member 360, for instance, by a bonding material, such as an electrically-conductive epoxy, disposed within the second via 380, between the connective element 740 and the second conductive material 400, wherein the bonding material may be applied to the individual connective element 740, prior to insertion thereof into the second via 380. In this manner, the spacing between the connective element 740 and the end wall 760 may be maintained. In other instances, the connective element 740 may be bonded to the support member 360 with a bonding material 800, such as an electrically-conductive epoxy, engaged therebetween and externally to the second via 380. More particularly, the bonding material 800 may be applied around the connective element 740 on the surface of the support member 380, outside the second via 380, such that bonding material 800 is in electrically-conductive engagement between the connective element 740 and the second conductive material 400. In some aspects, the bonding material 800 is applied so as to not contaminate any adjacent pMUT devices by entering the second vias thereof, particularly in instances where the second vias are electrically isolated from each other.

In some instances, as shown in FIG. 12, the connective element 740 may be engaged with a connection support substrate 820, with the connective element 740 inserted into and extending through a third via 840 defined by the connection support substrate 820, prior to the connective element 740 being bonded to the support member 360, wherein the connection support substrate 820 may be previously etched to define the third via 840 extending therethrough. In still other instances, as shown in FIG. 13, an acoustic member 860 may also be engaged with the connection support substrate 820, whereby the acoustic member 860 may likewise define an acoustic member via 880 corresponding to the third via 840 defined by the connection support substrate 820, prior to engaging the connective element 740 with the connection support substrate 820. As such, the connective element 740 may be inserted into and extend through the third via 840 defined by the connection support substrate 820 and the acoustic member via 880 defined by the acoustic member 860, prior to bonding the connective element 740 to the support member 360. In such instances, the acoustic member 860 may be selected according to appropriate acoustic dampening properties, so as to provide desirable acoustic dampening for the pMUT transducer array (i.e., so as to inhibit or prevent vibrations from the piezoelectric material from reverberating back to the piezoelectric material). In other aspects, the connective element 740 may be inserted into at least one of the support member 360 and connection support substrate 820. In such instances, the acoustic member 860 may comprise, for example, a polymer material in a fluid/liquid state that may be backfilled into the gap between the connection support substrate 820 and the support member 360, and between the connective elements 740, wherein the fluid/liquid polymer may then be cured to form the acoustic member 860.

Another aspect of the present disclosure is directed to the engagement of one or more of the connective elements with the connection support substrate (or the pMUT transducer array) in instances involving the same. More particularly, such aspects of the present disclosure are directed to facilitating and/or expediting the connective element/connection support substrate (or pMUT transducer array) engagement process. In some exemplary instances, the pitch of pMUT transducer devices in a transducer array may be on the order of between about 100 μm and about 200 μm, while the diameter of a corresponding connective element (e.g., wire) is on the order of about 50 μm. As such, precise alignment of the connective element with the connection support substrate is a consideration in the manufacturing process.

FIG. 14 thus schematically illustrates one aspect of the present disclosure directed to the assembling of a 2D array of connective elements (i.e., wires) 900 with respect to the connection support substrate or the pMUT transducer array (see, generally, element 920). In one instance, a guide substrate 940, about as wide as one dimension of connection support substrate/transducer array 920, may be configured so as to define a plurality of parallel, spaced-apart channels 960 extending across the width thereof (and extending along the length of the guide substrate 940), wherein the spacing of the channels 960 corresponds to the spacing of the third vias defined by the connection support substrate and/or the spacing of the second vias of the pMUT devices in the transducer array. In some aspects, the guide substrate 940 may be comprised of silicon, and the channels 960 may be "V" shaped. The "V" shape of the channels 960 formed, for example, by anisotropic crystallographic etching of the silicon, may promote, for instance, alignment of the connective elements 900 with respect to the desired spacing therebetween. Once the connective elements 900 are laid in the respective channels 960, so as to extend longitudinally outward thereof, a retaining member 980 may be removably applied over the channels 960 so as to retain the connective elements 900 within the channels 960. Once prepared, the guide substrate 940 may be disposed adjacent to the intended connection support substrate/pMUT transducer array 920 (i.e., using micropositioners), and the connective elements 900 slid or otherwise longitudinally directed along the channels 960 to engage the intended connection support substrate/pMUT transducer array 920. In some instances, the channels 960 (and the retaining member 980, if necessary) may have an anti-stiction coating (e.g., fluoropolymer) applied thereto to inhibit or prevent electrostatic attraction with the connective elements 900. Upon bonding the connective elements 900, as necessary, the retaining member 980 and the guide substrate 940 may be removed, leaving the connective elements 900 engaged with the intended connection support substrate/pMUT transducer array 920. As shown, the guide substrate 940/retaining member 980 may be configure to address one row (or column) of the 2D transducer array at a time. As such, repeat application of the disclosed process may be required in order to populate the 2D transducer array with an appropriate complement of connective elements 900.

In addition to such an assembly process for individual connective elements, as disclosed above, another aspect of the present disclosure may be directed to direct integration of a suitable assembly of connective elements. In this regard, some aspects may be directed to forming the connective elements 1000 in an appropriate carrier matrix 1020. For example, as schematically shown in FIG. 15, nanofibers could be formed in the channels of the guide substrate and, if necessary, plated with a conductive material to produce a conducting "cable." In other instances, a monolithic cable may be attained by fabricating, for example, by a co-extrusion process, a flexible composite assembly having the connective elements arranged in a polymeric matrix. For example, one such configuration may include, for example, a co-extrusion of a doped PET polymer (i.e., having a resistivity of about 5 Ohm-cm or less, such as, for instance, about 20 μOhm-cm) in an insulator matrix comprised of undoped PET or polypropylene. In one desirable instance, the connective elements may each have a resistance of less than about 20 Ohms. Once formed, one end of the monolithic cable aspect may be polished (i.e., perpendicularly to the longitudinal axis) so as to provide a planar surface for bonding with an appropriate bonding material to the pMUT transducer array, as shown in FIG. 16. In particular instances, the polymer used for the insulator matrix may be selected according to acoustic dampening properties, so as to provide desirable acoustic dampening for the pMUT transducer array (i.e., so as to inhibit or prevent vibrations from the piezoelectric material from reverberating back to the piezoelectric material).

Many modifications and other aspects of the disclosures set forth herein will come to mind to one skilled in the art to which these disclosures pertain having the benefit of the teachings presented in the foregoing descriptions and the associated drawings. For example, the exemplary methods and aspects thereof as disclosed herein may also have related apparatuses associated therewith, as otherwise disclosed herein. Further, the pMUT transducer devices disclosed herein may, as necessary or desired, be engaged with an IC (e.g., a control IC such as amplifier or multiplexer), an interposer (e.g., silicon or flex cable), or a redistribution element, for example, using solder bumps, gold stud bumps, metal stud bumps, anisotropic conductive epoxy, or other suitable electrically-conductive connection provisions, to provide an electrically-conductive engagement between the second conductive material of a particular pMUT transducer device and the IC, flex cable, cable assembly, interposer, or redistribution element. In addition, in some of the exemplary methods disclosed herein, a bonding material may sometimes be engaged with the support member so as to extend across the second vias defined thereby. In those instances, a suitably selected material comprising the bonding material may allow the bonding material to desirably function as an acoustic dampener for absorbing and/or dissipating vibrations emitted from the piezoelectric material, thereby inhibiting or preventing reverberation of the piezoelectric material along the second via. As such, the apparatuses and methods disclosed herein may be suitably adapted to address such instances, within the scope of the present disclosure. Therefore, it is to be understood that the disclosures are not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A piezoelectric ultrasonic transducer apparatus, comprising:
 a transducer device disposed on a dielectric layer on a device substrate, and including a piezoelectric material disposed between a first electrode and a second electrode, the device substrate and the dielectric layer defining a first via extending to the first electrode and substantially filled with a first conductive material, the transducer device further including a support member engaged with the device substrate and the first conductive material, and defining a second via extending thereto, the second via having a second conductive material disposed thereon and forming an electrically-conductive engagement with the first conductive material, the second conductive material extending outwardly of the second via so as to be accessible externally to the support member; and
 a connective element extending through a third via defined by a connection support substrate and being in electrically-conductive engagement with the second conductive material, with one of the connective element and the connection support substrate being bonded to one of the support member and the second conductive material by a bonding material engaged therebetween.

2. An apparatus according to claim 1, wherein the connection support substrate is bonded to the support member with a non-conductive bonding material engaged therebetween.

3. An apparatus according to claim 1, wherein the connective element is bonded to the second conductive material with one of a conductive epoxy, a conductive solder element, a conductive stud element and an anisotropically-conductive epoxy engaged therebetween.

4. An apparatus according to claim 1, wherein the connective element is bonded to the connection support substrate with a non-conductive epoxy engaged therebetween and externally to the third via.

5. An apparatus according to claim 1, further comprising an integrated circuit device interposed between the one of the connective element and the connection support substrate and the one of the support member and the second conductive material, the integrated circuit device being in electrically-conductive engagement with at least the connective element and the second conductive material, or being configured to facilitate an electrically-conductive engagement at least between the connective element and the second conductive material by way of a conductive element extending therethrough in a device via defined thereby.

6. A piezoelectric ultrasonic transducer apparatus, comprising:
 a transducer device disposed on a dielectric layer on a device substrate, and including a piezoelectric material disposed between a first electrode and a second electrode, the device substrate and the dielectric layer defining a first via extending to the first electrode and substantially filled with a first conductive material, the transducer device further including a support member engaged with the device substrate and the first conductive material, and defining a second via extending thereto, the second via having a second conductive material disposed thereon and forming an electrically-conductive engagement with the first conductive material about an end wall of the second via; and
 a connective element received into the second via defined by the support member and bonded to the support member by a bonding material engaged therebetween, the connective element being in electrically-conductive engagement with the second conductive material and spaced apart from the end wall of the second via.

7. An apparatus according to claim 6, wherein the second conductive material is accessible externally to the support member.

8. An apparatus according to claim 6, wherein the bonding material comprises an electrically-conductive epoxy further engaged between and in electrically-conductive engagement with the connective element and the second conductive material, externally to the second via.

9. An apparatus according to claim 6, further comprising a connection support substrate defining a third via having the connective element inserted into and extending therethrough.

10. An apparatus according to claim 9, further comprising an acoustic member engaged with the connection support substrate, the acoustic member defining an acoustic member via corresponding to the third via, and having the connective element inserted into and extending therethrough.

* * * * *

UNITED STATES PATENT AND TRADEMARK OFFICE
CERTIFICATE OF CORRECTION

PATENT NO. : 8,624,469 B2
APPLICATION NO. : 13/643649
DATED : January 7, 2014
INVENTOR(S) : David Dausch et al.

It is certified that error appears in the above-identified patent and that said Letters Patent is hereby corrected as shown below:

In the Specification

In Column 1, before the heading "BACKGROUND OF THE DISCLOSURE", please add the following heading and paragraph:
FEDERALLY SPONSORED RESEARCH OR DEVELOPMENT
This invention was made with government support under R33 EB000566 awarded by the National Institutes of Health. The government has certain rights in the invention.

Signed and Sealed this
Eighth Day of August, 2023

Katherine Kelly Vidal
*Director of the United States Patent and Trademark Office*